US00PP26628P3

(12) United States Plant Patent
Apps

(10) Patent No.: US PP26,628 P3
(45) Date of Patent: Apr. 19, 2016

(54) DAYLILY PLANT NAMED 'HAPPY DAYS ARE HERE AGAIN'

(50) Latin Name: *Hemerocallis hybrida*
Varietal Denomination: Happy Days Are Here Again

(71) Applicant: BlewLine Nursery, Inc., Bridgeton, NJ (US)

(72) Inventor: Darrel A. Apps, Wild Rose, WI (US)

(73) Assignee: BLEWLINE NURSERY, INC., Bridgeton, NJ (US)

( * ) Notice: Subject to any disclaimer, the term of this patent is extended or adjusted under 35 U.S.C. 154(b) by 78 days.

(21) Appl. No.: 14/121,519

(22) Filed: Sep. 15, 2014

(65) Prior Publication Data

US 2016/0081250 P1 Mar. 17, 2016

(51) Int. Cl.
*A01H 5/02* (2006.01)

(52) U.S. Cl.
USPC ..... Plt./312

(58) Field of Classification Search
USPC ..... Plt./312
See application file for complete search history.

*Primary Examiner* — Anne Grunberg
(74) *Attorney, Agent, or Firm* — Buchanan Ingersoll & Rooney PC

(57) ABSTRACT

A new and distinct *Hemerocallis* cultivar of the dormant type is provided. The new cultivar is very floriferous and forms attractive ruffled clean light yellow flowers displaying substantial substance, and a funnel-shaped form over an extended period of time. In U.S.D.A. Hardiness Zone No. 6, blooming commonly begins during late June and commonly ends in mid-September. The new cultivar displays a plurality of fans and a plurality of scapes per fan. In excess of 12 buds commonly are formed per scape. The new cultivar is well suited for growing as distinctive colorful ornamentation in the landscape.

2 Drawing Sheets

Botanical/commercial classification: *Hemerocallis hybrida*/Daylily.

Varietal denomination: cv. Happy Days Are Here Again.

SUMMARY OF THE INVENTION

The present invention comprises a new and distinct cultivar of *Hemerocallis* plant of the dormant type, and hereinafter is referred to by the cultivar name 'Happy Days Are Here Again'.

The new cultivar is the product of a planned breeding program which had as its objective the creation of a new Daylily cultivar that is intended for use as attractive ornamentation in the landscape.

The cross that resulted in the production of the new cultivar of the present invention was carried out in a controlled environment during May, 2006, at Bridgeton, N.J., U.S.A. The female parent (i.e., the seed parent) of the new cultivar was the 'Early And Often' cultivar (non-patented in the United States) which displays dull orange flowers. Such female parent is registered with the American *Hemerocallis* Society.

The male parent (i.e., the pollen parent) of the new cultivar was an unnamed seedling (non-patented in the United States) that was the product of the cross of a pair of unnamed and unreleased *Hemerocallis* plants (non-patented in the United States) displaying yellow flowers of less than optimum substance.

The parentage of the new cultivar of the present invention can be summarized as follows:

'Early And Often'×Unnamed Seedling.

The seeds resulting from the above pollination were sown and small plantlets were obtained which were physically and biologically different from each other. A number of such plants were transplanted into the field at Bridgeton, N.J., U.S.A., during June 2007. Selective study during May-June 2008 resulted in the identification of a single plant of the new cultivar.

It was found that the new *Hemerocallis* plant of the present invention is of the dormant type:

(a) forms attractive ruffled clean light yellow flowers having substantial substance, and a funnel-shaped form,
(b) possesses a long blooming season with substantially multiple repeat blooming,
(c) exhibits a propensity to readily display a plurality of fans, and
(d) readily forms a plurality of scapes per fan over the flowering season.

The 'Happy Days Are Here Again' cultivar resembles some well-known cultivars, such as the 'Stella D' Oro' cultivar (non-patented in the United States) and the 'Happy Returns' cultivar (non-patented in the United States) in the sense that it commonly possesses an unusually long and substantially continuous blooming season (i.e., a multiple repeat character) of up to approximately 90 days in U.S.D.A. Hardiness Zone No. 6. Such blooming commonly begins during late June and commonly ends in mid-September. This compares to a bloom period of less than about 30 days for over 99 percent of the hybrid Daylilies that presently are available in the trade.

As indicated, the 'Happy Days Are Here Again' plant exhibits attractive ruffled clean yellow flowers. Such flowers can be readily distinguished from the orange-yellow flowers of the 'Stella D' Oro' cultivar, and the medium yellow flowers of the 'Happy Returns' cultivar. To the best knowledge of the originator, the 'Happy Days Are Here Again' cultivar is the first long and substantially continuously blooming Daylily having flowers that exhibit such a clean light yellow hue combined with substantial flower substance on a substantial scape.

The new cultivar can form up to 8 or more fans per year. This compares to approximately 6 to 8 fans per year for the 'Stella D' Oro' cultivar and the 'Happy Returns' cultivar. Most Daylily cultivars form only approximately 2 to 3 fans per year. Also, the new cultivar commonly forms several scapes per fan during the flowering season, unlike most Daylilies that commonly produce only one scape per fan.

Asexual reproduction of the new cultivar by division was initially carried out on Sep. 1, 2008 at Bridgeton, N.J., U.S.A. At the time of such asexual reproduction the original plant of the new cultivar consisted of a clump of eight fans that were phenotypically identical to each other. More specifically, the clump of the new cultivar was removed from the field and the fans were divided. It has been demonstrated that the characteristics of the new cultivar are firmly fixed and are well retained following this asexual reproduction.

The 'Happy Days Are Here Again' plant has not been observed under all possible environmental conditions to date. Accordingly, it is possible that the phenotype may vary somewhat with variations in the environment, such as temperature, light, day length, contact with pesticides, etc.

The new 'Happy Days Are Here Again' cultivar will be marketed by the Assignee under the HAPPY EVER APPSTER trademark beginning in May 2015.

BRIEF DESCRIPTION OF THE PHOTOGRAPHS

The accompanying photographs show the original plant of the new cultivar in color as nearly true as it is possible to make the same in color illustrations of this character. Each photograph was prepared on Jun. 11, 2013 while the plant was being grown at Bridgeton, N.J., U.S.A. The attractive ruffled pure yellow flowers are illustrated as well as foliage, and reproductive parts.

DETAILED BOTANICAL DESCRIPTION

Figure 1:
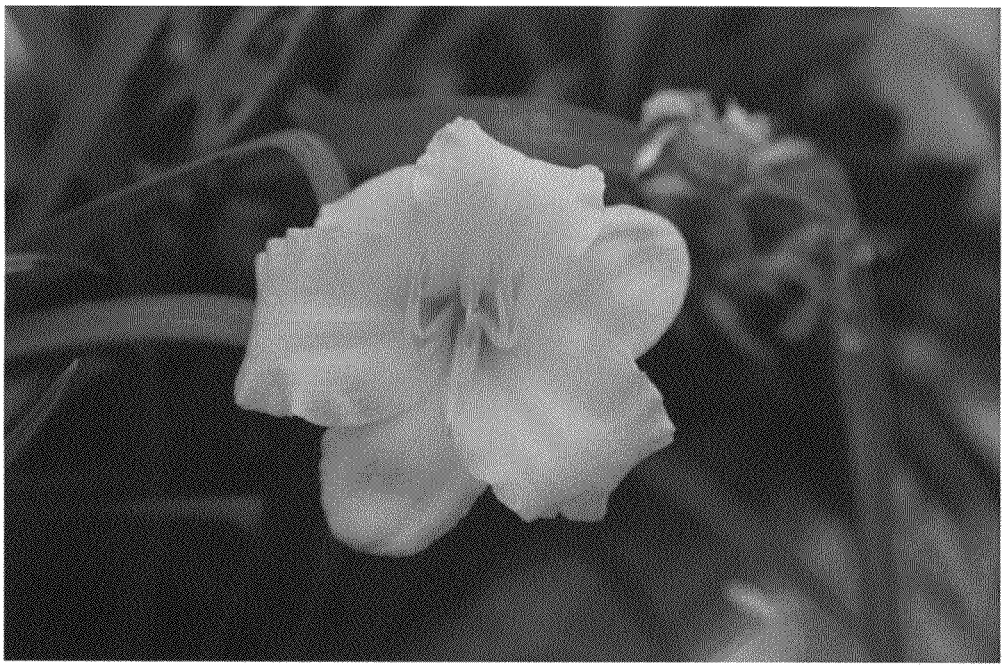
FIG. 1 illustrates a close view of a clean yellow opened flower.
Figure 2:
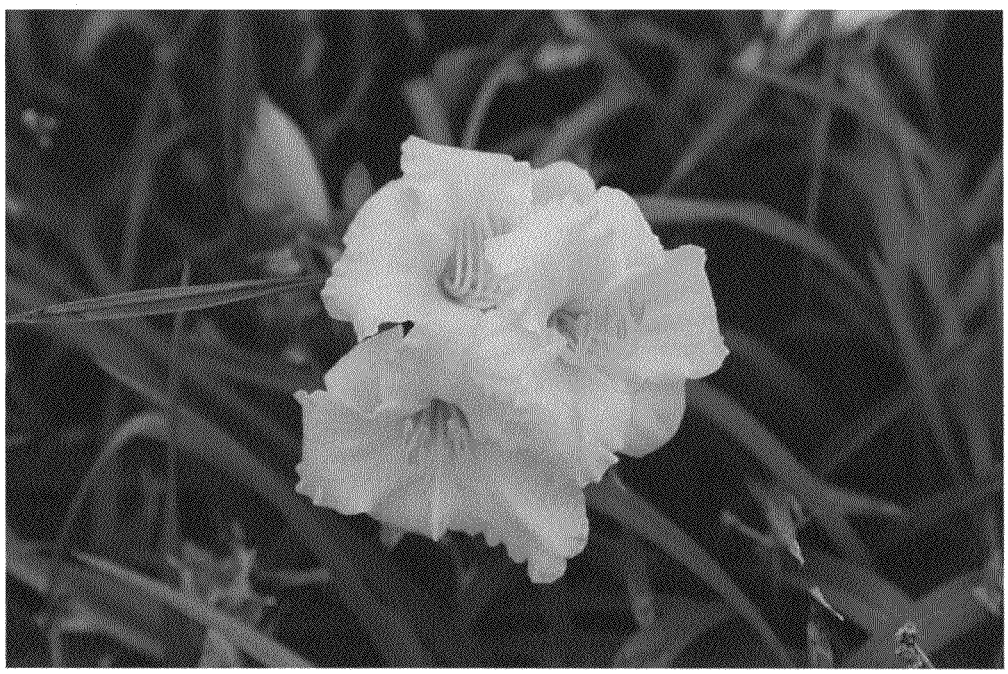
FIG. 2 illustrates a cluster of clean yellow opened flowers.

The chart used in the identification of the colors described herein is The R.H.S. Colour Chart of The Royal Horticultural Society, London, England (1995 Edition or equivalent). The original plant of the new cultivar is described, except as otherwise indicated, when observed and described during August 2014 while growing at Bridgeton, N.J., U.S.A., under field growing conditions.

Classification:

*Botanical.*—*Hemerocallis hybrida.*

*Commercial name.*—Daylily.

*Cultivar.*—Happy Days Are Here Again.

Plant:

*Height.*—Approximately 33 cm at an age of one year.

*Width.*—Approximately 41 cm at an age of one year.

*Foliage.*—Form: single stem, substantially erect fan-shaped plant having narrow arching, long, keeled, grass-like glabrous to slightly textured leaves that are two-ranked at the base of the scape. Quantity: abundant, with a mature plant commonly having approximately 16 leaves per fan. Leaf Size: commonly approximately 1.2 cm in width on average, and approximately 39 cm in length on average. Leaf Shape: sessile, linear and long-keeled with entire margins, and a sharply acuminate apex. Leaf Variation: on the upper surface commonly faint and near Yellow-Green Group 147A in coloration, and on the under surface strongly keeled at the mid-rib and near Yellow-Green Group 147A in coloration. Texture: glabrous. Color: Yellow-Green Group 146A on both surfaces. Type: dormant with the plant commonly retaining substantially no green coloration during the winter in U.S.D.A. Hardiness Zone No. 6b.

*Scape.*—Color: near Yellow-Green Group 146A. Length: commonly approximately 43 cm on average. width: commonly approximately 5 mm on average.

*Disease resistance.*—Typical of *Hemerocallis* with no problems having been observed to date.

Inflorescence:

*Bud.*—Form: modified oblanceolate slightly tapered cylindrical shape. Apex: upper quarter comes to a point. Size: on the day prior to opening commonly approximately 6.5 cm in length on average, and approximately 2 cm in width on average. Number: commonly in excess of 12 per scape. Color: near Yellow-Green Group 151B. Opening Rate: commonly approximately three hours on average.

*Peduncle.*—Length: commonly approximately 5 mm on average. Width: commonly approximately 3 mm on average. Strength: tends to be rigid and sturdy. Color: near Yellow-Green Group 144A.

*Flower.*—Size: commonly has a diameter of approximately 9 cm on average and a depth of approximately 5 cm on average. Borne: singly on the branchlets of a sturdy erect rachis which is ramulose. Each scape commonly has at least 10 peduncles, each of which commonly divides into approximately 2 pedicels. Blooms Per Scape: commonly approximately 1 or 2 each day. Tepalage: each flower consists of six perianth segments wherein there are three outer tepals and three inner tepals all in an imbricated arrangement. Outer Tepal Shape: oblanceolate with slightly undulated entire margins and an acuminate apex. Outer Tepal Texture: slightly ribbed. Outer Tepal Size: commonly approximately 6 cm in length on average, and approximately 2.5 cm in width on average. Outer Tepal Color: the outer surface is near Yellow-Green Group 151B changing to Yellow-Green Group N144B at the base, and the inner surface is near Yellow-Group 5D changing to near Yellow-Green Group N144A at the base. Inner Tepal Texture: with a slightly ruffled edge. Inner Tepal Size: commonly approximately 6.5 cm in length on average, and approximately 4 cm in width on average. Inner Tepal Color: the outer surface is near Yellow Group 5C changing to near Yellow-Green Group N144B at the base, and the inner surface is near Yellow Group 3C changing to near Yellow-Green Group N144B at the base. Eyezone: none. Blooming Habit: the flowers commonly bloom substantially continuously and the scape commonly is substantially continuously in bloom for up to approximately 90 days per year in Hardiness Zone No. 6. Effects of Weather: the flowers will withstand rain damage in view of the strength of the tepals. Lasting Quality: commonly at least 16 hours. As with other *Hemerocallis* cultivars known to the inventor, the flower color eventually fades somewhat during the day with the natural effects of environmental conditions and ongoing maturity. Fragrance: none.

*Reproductive organs*.—Stamen Number: six per flower. Stamen Disposition: individually inserted at the summit of the perianth tube. Anther Disposition: introrse. Anther Size: approximately 5 mm in length. Anther Color: difficult to characterize in view of small size, and is believed to be near Yellow-Green Group 150C. Filament Configuration: slender. Filament Length: commonly approximately 4 cm on average. Filament Color: near Yellow-Green Group 154C. Pollen Color: near Grey-Orange Group N163C. Pistil Number: one per flower. Style Length: approximately 6 cm on average. Style Color: near Yellow-Green Group 154C. Stigma Color: near Yellow-Green Group 154C. Ovaries: three-celled, oblong, becoming a loculiedally three-valved capsule, and near Yellow-Green Group 149A in coloration.

*Fruit*.—Configuration: the seed pod is in the form of an ovoid capsule. Color: at maturity commonly is near Yellow-Green Group 146A. Fertility: the seeds are fertile.

Hardiness: Cold tolerance is displayed in U.S.D.A. Hardiness Zone No. 4a, and heat tolerance is displayed in U.S.D.A. Hardiness Zone No. 8b.

I claim:

1. A new and distinct cultivar of *Hemerocallis* plant of the dormant type, which:

(a) forms attractive ruffled clean light yellow flowers having substantial substance, and a funnel-shaped form, (b) possesses a long blooming season with substantially multiple repeat blooming, (c) exhibits a propensity to readily display a plurality of fans, and (d) readily forms a plurality of scapes per fan over the flowering season;

substantially as illustrated and described.

* * * * *